(12) United States Patent
Singh et al.

(10) Patent No.: US 12,607,597 B2
(45) Date of Patent: Apr. 21, 2026

(54) PORTABLE ELECTROCHEMICAL NUTRIENT TESTING DEVICE FOR SOIL HEALTH MONITORING

(71) Applicant: Rajul Sachin Patkar, Mumbai (IN)

(72) Inventors: Mukul Singh, Prayagraj (IN); Rajul Sachin Patkar, Mumbai (IN); Madhuri Vinchurkar, Mumbai (IN)

( * ) Notice: Subject to any disclaimer, the term of this patent is extended or adjusted under 35 U.S.C. 154(b) by 182 days.

(21) Appl. No.: 18/290,956

(22) PCT Filed: Sep. 20, 2022

(86) PCT No.: PCT/IN2022/050837
§ 371 (c)(1),
(2) Date: Jan. 22, 2024

(87) PCT Pub. No.: WO2023/047410
PCT Pub. Date: Mar. 30, 2023

(65) Prior Publication Data
US 2024/0353370 A1 Oct. 24, 2024

(51) Int. Cl.
*G01N 27/416* (2006.01)
*G01N 27/30* (2006.01)
(Continued)

(52) U.S. Cl.
CPC ....... *G01N 27/4161* (2013.01); *G01N 27/302* (2013.01); *G01N 27/308* (2013.01);
(Continued)

(58) Field of Classification Search
CPC ............ G01N 27/4161; G01N 27/302; G01N 27/308; G01N 27/333; G01N 27/327;
(Continued)

(56) References Cited

U.S. PATENT DOCUMENTS

| | | | |
|---|---|---|---|
| 8,767,194 B2 * | 7/2014 | Preiner | G01N 21/31 |
| | | | 356/244 |
| 2012/0181184 A1 * | 7/2012 | Whitesides | B01L 3/502 |
| | | | 204/400 |

(Continued)

FOREIGN PATENT DOCUMENTS

| | | | | |
|---|---|---|---|---|
| IN | 202021057257 A | * | 1/2021 | |
| WO | WO 2020182830 A1 | * | 9/2020 | G01N 27/30 |

OTHER PUBLICATIONS

Hamedi et al., "Integrating Electronics and Microfluidics on Paper," Adv. Mater. 2016, 28, 5054-5063 (Year: 2016).*

(Continued)

*Primary Examiner* — Alexander S Noguerola
(74) *Attorney, Agent, or Firm* — Novel Patent Services LLC

(57) ABSTRACT

The present disclosure proposes a portable, battery operated, calibration free, soil independent electrochemical nutrient testing device for soil health monitoring that is designed for in-field nutrient analysis and aids to monitor soil health accurately on a regular basis. The portable electrochemical nutrient testing device for soil health monitoring, comprises a function generator block, at least one screen-printed electrochemical sensor, working electrode, counter electrode, reference electrode, plurality of contact pads, voltage control module, data acquisition module, micro-controller unit, display unit, a processing module, and a location intelligence module. The portable electrochemical nutrient testing device doesn't require prior conditioning and calibration of the electrodes and does not require complex sample preparation using multiple reagents.

8 Claims, 8 Drawing Sheets

| (51) | Int. Cl. | |
|---|---|---|
| | *G01N 27/333* | (2006.01) |
| | *G01N 27/403* | (2006.01) |
| | *G01N 33/18* | (2006.01) |
| | *G01N 33/24* | (2006.01) |

(52) U.S. Cl.
CPC ....... *G01N 27/333* (2013.01); *G01N 27/4035* (2013.01); *G01N 33/188* (2013.01); *G01N 33/245* (2024.05)

(58) Field of Classification Search
CPC ..... G01N 27/3272; G01N 33/18–1853; G01N 33/245; A01G 9/26; E02D 1/04; A01N 1/40; A01N 1/28
See application file for complete search history.

(56) References Cited

U.S. PATENT DOCUMENTS

| 2016/0270289 | A1* | 9/2016 | Schildroth | ............. | G01N 33/24 |
|---|---|---|---|---|---|
| 2016/0347426 | A1* | 12/2016 | Thompson | ............. | B63B 32/70 |
| 2017/0032258 | A1* | 2/2017 | Miresmailli | ............. | G06N 5/04 |
| 2019/0281771 | A1* | 9/2019 | Setton | ................. | B65G 1/0478 |
| 2020/0132655 | A1* | 4/2020 | Kusiek | ................. | G01N 27/333 |
| 2021/0016286 | A1* | 1/2021 | Swanson | ............. | G01N 1/4055 |
| 2022/0015287 | A1* | 1/2022 | Kramarenko | ........ | G05B 13/028 |

OTHER PUBLICATIONS

Rosenberg et al., "In-field determination of soil ion content using a handheld device and screen-printed solid-state ion-selective electrodes," PLOS One | https://doi.org/10.1371/journal.pone.0203862 Sep. 25, 2018 (Year: 2018).*

"Soil health card Scheme Completes 5 years on Feb. 19, 2020," India Ministry of Agriculture & Farmers Welfare (Year: 2020).*

* cited by examiner

300

Collect soil at 20cm depth

Sieve it

Add reagent to fine soil

Wait until soil settles

Connect test Strip to device

Put few drops of soil solution on strip

Get result in 30 sec

30s

Nutrisens

PORTABLE ELECTROCHEMICAL NUTRIENT TESTING DEVICE FOR SOIL HEALTH MONITORING

FIELD OF THE INVENTION

The present disclosure generally relates to agricultural technology, and more particularly to a portable electrochemical nutrient testing device for soil health monitoring that is designed for in-field nutrient analysis and aids to monitor soil health accurately on a regular basis.

BACKGROUND

Agriculture is the practice of cultivating plants and it is the basic source of food for all human beings. Plants are cultivated on various types of soils. Healthy soils lead to better productivity. To maintain healthy soils, precise amount of fertilizer is applied at right time and at right place depending on the soil and crop. Excess fertilizers are used to cultivate plants according to the needs which can change the properties of soil and causes soil acidification, heavy metals pollution, soil compaction and abnormal changes in soil micro biome. This results in soil degradation and drop in soil fertility, thereby rendering that soil useless for agriculture.

To keep soil healthy, periodic soil testing is essential. In general, farmers send soil samples to the agricultural labs in order to check soil's nutrient content. Sometimes, the farmers obtain improper results which result in excessive use of fertilizers. This excess use of fertilizers will leach into the ground water thereby contaminating it and harming the nearby resident's health. Soil also becomes infertile overtime, since golden ratio of the fertilizers is not maintained.

Conventionally, soil testing devices which help the farmers to evaluate the soil's nutrient values are bulky and utilize spectrophotometer or colorimetry-based soil testing methods and as a result, they require complex sample preparation which is time consuming and not accurate.

This conventional type of soil testing method is bulky and time-consuming and requires the complex sample preparation and a skilled person to perform soil testing. Therefore, there is a need for a portable and cost-effective soil testing device which is affordable, easy to use and accurate.

Current electrochemical devices utilize 2 electrode-based system in order to evaluate nutrients in the soil and requires complicated maintenance of those electrodes. The current electrochemical devices require calibration before every usage which is difficult and time-consuming for the farmers and can introduce errors.

Therefore, there exists a need to provide a nutrient testing device for soil health monitoring which is designed for in-field nutrient analysis and aids in monitoring soil health accurately on a regular basis. There is a need for a device that aids to repeatedly evaluate nutrient value of soil accurately within less time. There is a need to provide a bio degradable and paper-based screen-printed device for testing nutrient value of the soil. There is a need to provide a soil testing device which is cost-effective, portable and easy to use. There is a need to provide a system that is soil independent and is pre calibrated without having the need to calibrate in field.

SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key nor critical elements of all embodiments, nor delineate the scope of any or all embodiments.

The present disclosure, in one or more embodiments, relates to a portable electrochemical nutrient testing device for soil water and plant health monitoring is provided. The electrochemical nutrient testing device for soil, water and plant health monitoring is designed for in-field nutrient analysis and aids to monitor soil health accurately on a regular basis.

In one embodiment herein, the portable electrochemical nutrient testing device, comprises a function generator block, at least one screen-printed electrochemical sensor, a working electrode, a counter electrode, a reference electrode, plurality of contact pads, a voltage control module, a data acquisition module, a micro-controller unit, and a display unit. The electrochemical nutrient testing device is independent of type of the sample and calibration free.

In one embodiment herein, the function generator block attached to the electrochemical nutrient testing device configured to produce a change in voltage or current signal. At least one screen-printed electrochemical sensor configured to test analytes from nutrients derived from sample, comprising, the working electrode positioned inside an insulating area configured to perform electrochemical reaction when the sample comes in contact.

The counter electrode is placed in between the working electrode and a paper substrate configured to complete the circuit. In specific, the screen-printed electrochemical sensor is fabricated using a variety of conducting pastes according to the requirement of the user. The fabrication is performed using silver or silver chloride (Ag/AgCl) and carbon paste and is chemically modified to make it selective to pH, phosphate, nitrate, potassium, calcium, magnesium, iron, zinc, boron, sulphur, manganese, calcium carbonate, copper, soil pathogens.

In one embodiment herein, the reference electrode positioned in the screen-printed electrochemical sensor configured to provide a stable reference potential. In specific, plurality of contact pads connected to the working electrode, the counter electrode and the reference electrode. In specific, input waveform is applied between the working electrode the reference electrode and the current flows between the working electrode and the counter electrode.

In one embodiment herein, the voltage control module is connected to the function generator block by the screen-printed electrochemical sensor configured to maintain the potential generated by the function generator block at the working electrode. In specific, the voltage control module is a potentiostat. The voltage control module maintains potential at the working electrode with respect to the reference electrode of the screen-printed electrochemical sensor. The data acquisition module connected to the voltage difference controller configured to receive voltage signal from the voltage difference controller and filter out the higher-order harmonics.

In one embodiment herein, the micro-controller unit connected to the data acquisition module and configured with an analog-to-digital converter configured to receive, store and process the voltage signal as a sample value from the data acquisition module to obtain nutrient content of the sample based on specialized algorithms to identify the correct signal from the rest of the signal. In specific, the micro-controller unit captures faradaic portion by neglecting the capacitive current and qualifies and quantifies the analyte present in the sample.

In one embodiment herein, the display unit connected to the microcontroller configured to display obtain nutrient content of the sample, wherein a portable liquid crystal display (LCD) is used to display the soil, water or plant health. The processing module configured with location intelligence module and stores geographical conditions of a respective location and the processing module analyze the location intelligence data and the sample nutrient data to generate nutrient map. In specific, sample nutrient data includes information regarding quality of soil, water, plants or the like. The geographical location can also be captured by a mobile device connected to the device.

An embodiment of the first aspect, the invention provides a method to analyse sample using electrochemical nutrient testing device. At one step, a sample is collected from at least 20 cm deep. At one step, the collected sample is sieved using filter to prepare fine and filtered sample. At one step, reagent is added to the filtered sample in a test tube to prepare a homogenous mixture. At one step, few drops of the homogenous mixture is gathered onto a test strip and connecting the test strip to the electrochemical nutrient testing device.

At one step, waiting for approximately 30 seconds to obtain nutrient parameters and the electrochemical nutrient testing device is connected to a mobile application. At one step, 2-way communication is enabled between the electrochemical nutrient testing device and mobile application and the parameters are uploaded from the mobile application into a cloud server.

At one step, the recommendations are identified and processed using artificial intelligence and machine learning wherein the processing employs artificial intelligence and machine learning computational methods to analyse the soil health and finally, the recommendations are given to user in the form of soil health card using the parameters calculated on the cloud server.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF DRAWINGS

The accompanying drawings, which are incorporated in and constitute a part of the specification, illustrate an embodiment of the invention, and, together with the description, explain the principles of the invention.

DETAILED DESCRIPTION

Figure 1:
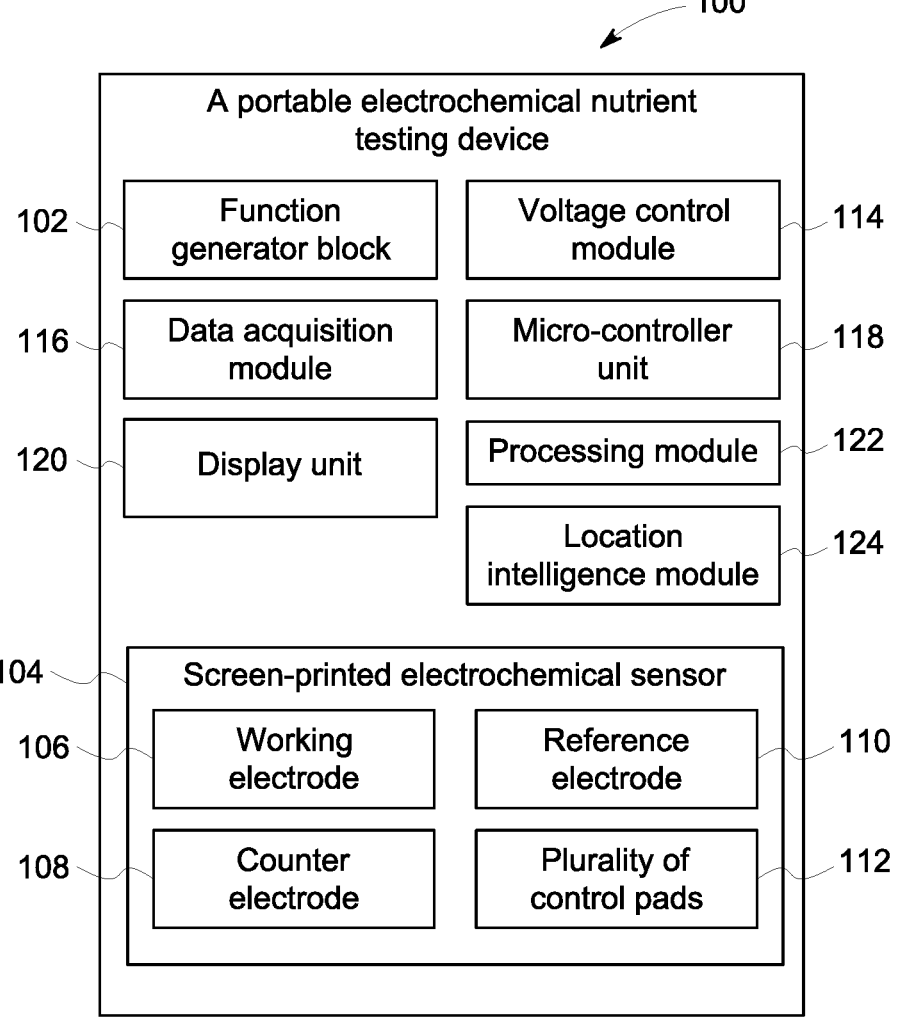
FIG. 1 illustrates an exemplary portable electrochemical nutrient testing device for soil, water and plant health monitoring in accordance with an exemplary embodiment of the invention.

Reference will now be made in detail to the present preferred embodiments of the invention, examples of which are illustrated in the accompanying drawings. Wherever possible, the same reference numerals are used in the drawings and the description to refer to the same or like parts.

Disclosed herein is a portable electrochemical nutrient testing device for soil, water and plant health monitoring is provided. The electrochemical nutrient testing device for soil, water and plant health monitoring is designed for in-field nutrient analysis and aids to monitor soil health accurately on a regular basis.

FIG. 1 refers to an exemplary portable electrochemical nutrient testing device for soil, water and plant health monitoring. The portable electrochemical nutrient testing device 100, comprises a function generator block 102, at least one screen-printed electrochemical sensor 104, a working electrode 106, a counter electrode 108, a reference electrode 110, plurality of contact pads 112, a voltage control module 114, a data acquisition module 116, a microcontroller unit 118, a display unit 120, processing module 122, and a location intelligence module 124. The electrochemical nutrient testing device 100 is independent of type of the sample and calibration free.

In one embodiment herein, the function generator block 102 attached to the electrochemical nutrient testing device 100 configured to produce a change in voltage or current signal. At least one screen-printed electrochemical sensor 104 configured to test analytes from nutrients derived from sample, comprising, the working electrode 106 positioned inside insulating area configured to perform electrochemical reaction when the sample comes in contact.

In one embodiment herein, the counter electrode 108 placed in between the working electrode 106 and a paper substrate configured to complete the circuit. In specific, the screen-printed electrochemical sensor 104 is fabricated using variety of conducting pastes according to the requirement of the user. The fabrication is performed using silver or silver chloride (Ag/AgCl) and carbon paste and is modified to make it selective to analyte under test according to the user requirements.

In one embodiment herein, the reference electrode 110 positioned in the screen-printed electrochemical sensor 104 configured to provide a stable reference potential. In specific, plurality of contact pads 112 connected to the working electrode 106, the counter electrode 108 and the reference electrode 110. In specific, input waveform is applied between the working electrode 106 the reference electrode 110 and the current flows between the working electrode 106 and the counter electrode 108.

In one embodiment herein, the voltage control module 114 connected to the function generator block 102 by the screen-printed electrochemical sensor 104 configured to maintain potential generated by the function generator block 102 at the working electrode 106. In specific, the voltage control module 114 is a potentiostat. The voltage control module 114 maintains potential at the working electrode 106 with respect to the reference electrode 110 of the screen-printed electrochemical sensor 104. The data acquisition module 116 connected to the voltage difference controller configured to receive voltage signal from the voltage difference controller and filter out the higher-order harmonics.

In one embodiment herein, the micro-controller unit 118 connected to the data acquisition module 116 and configured with an analog-to-digital converter configured to receive, store and process the voltage signal as a sample value from the data acquisition module 116 to obtain nutrient content of the sample. In specific, the micro-controller unit 118 captures faradaic portion by neglecting the capacitive current and qualifies and quantifies the analyte present in the sample.

In one embodiment herein, the display unit 120 connected to the microcontroller unit 118 configured to display obtain nutrient content of the sample, wherein a portable liquid crystal display (LCD) is used to display the soil, water or plant health parameters. The processing module 122 configured with location intelligence module 124 and stores geographical conditions of a respective location and the processing module analyze the location intelligence data and the sample nutrient data to generate nutrient map. In specific, sample nutrient data includes information regarding quality of soil, water and plants or the like.

Figure 2:
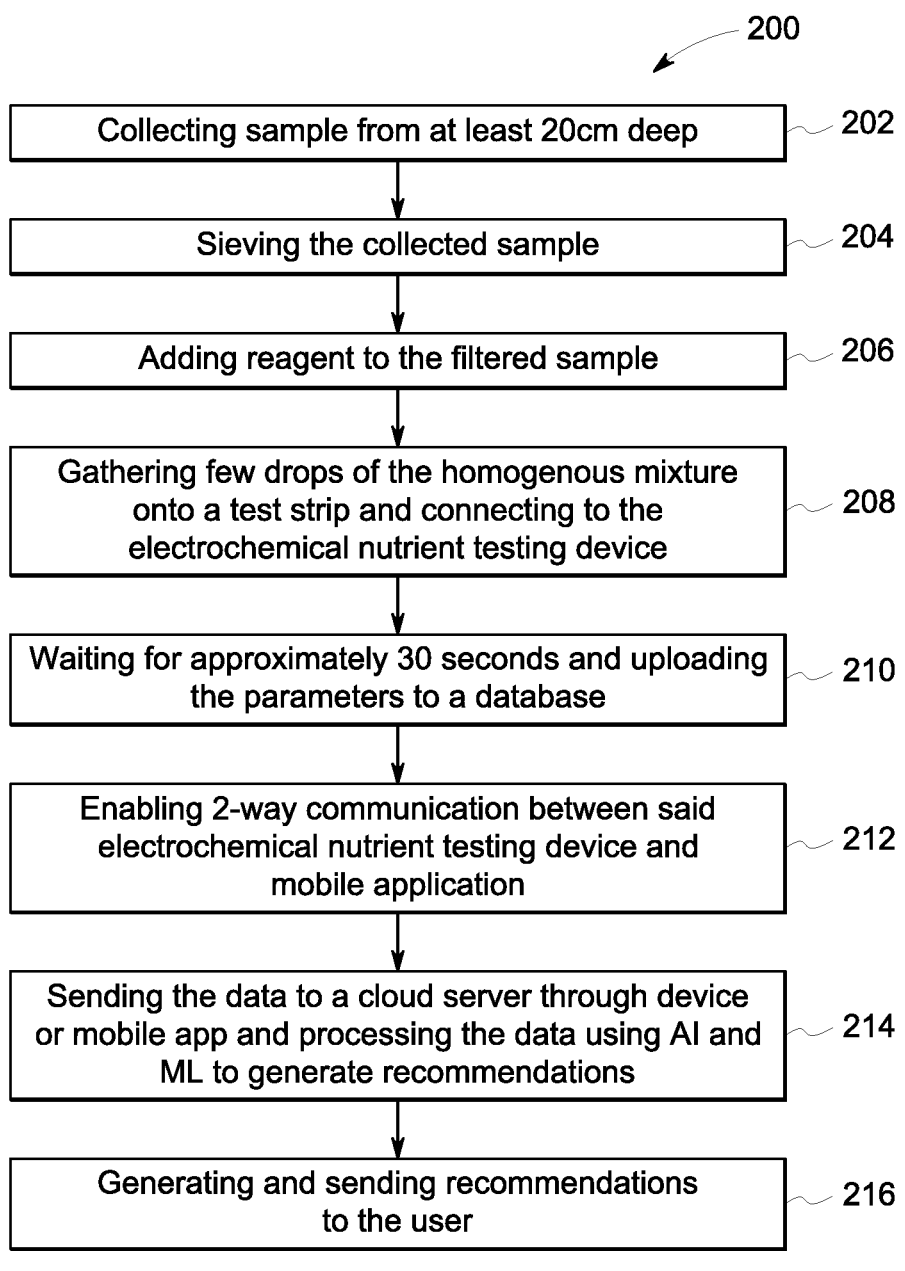
FIG. 2 illustrates an exemplary method to analyse sample using electrochemical nutrient testing device in accordance to an exemplary embodiment of the invention.

FIG. 2 refers to a flowchart of a method 200 to analyse sample using electrochemical nutrient testing device. The method 200 to analyse sample using electrochemical nutrient testing device, comprises the steps of, firstly, at step 202, sample is collected from at least 20 cm deep. Later, the collected sample is sieved using filter to prepare fine and filtered sample, at step 204. Then, at step 206, reagent is added to the filtered sample in a test tube to prepare a homogenous mixture. Later, at step 208, a few drops of the homogenous mixture is gathered onto a test strip and connecting the test strip to the electrochemical nutrient testing device.

At step 210, waiting for approximately 30 seconds to obtain nutrient parameters and the electrochemical nutrient testing device is connected to a mobile application. Then, at step 212, 2-way communication is enabled between the electrochemical nutrient device and mobile application and the parameters are uploaded from the mobile application into a cloud server. At step 214, the data is sent to a cloud server through device or mobile app and the data is processed using Artificial Intelligence and Machine Learning to generate recommendations. Finally, at step 216, recommendations are generated and sent to the user from the cloud server to the mobile application for remote monitoring and crop management by the user.

Figure 3:
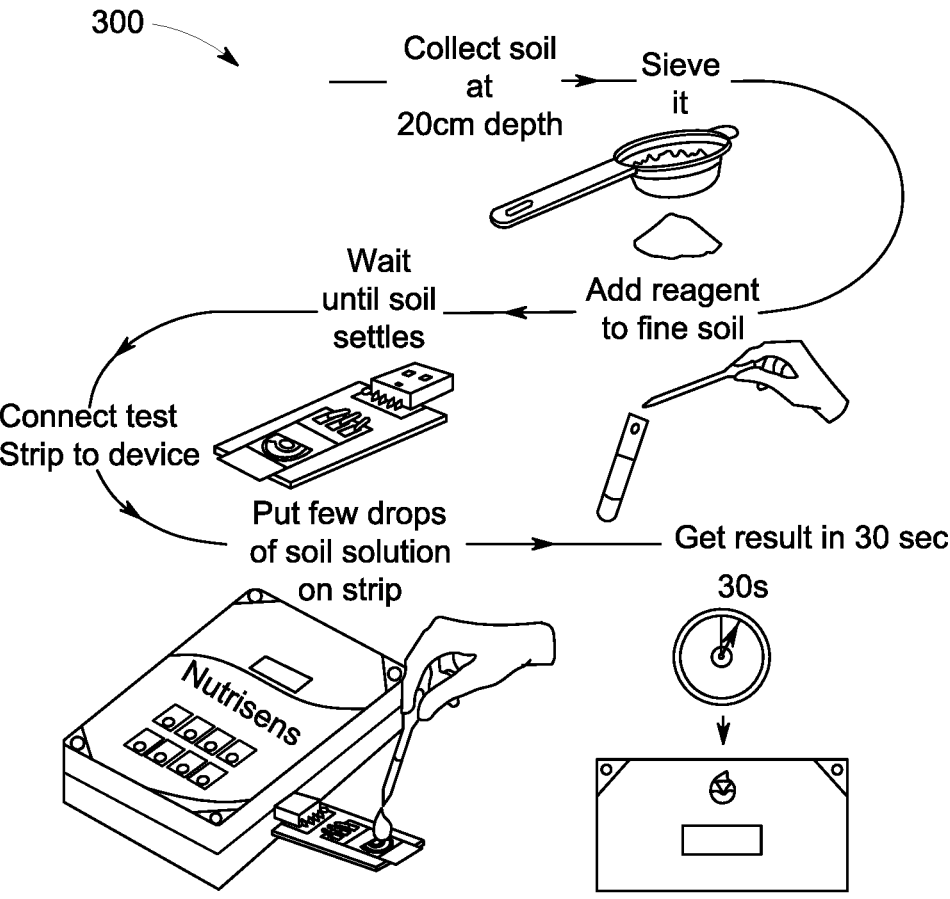
FIG. 3 illustrates an exemplary flowchart of working principle of portable electrochemical nutrient testing device in accordance to an exemplary embodiment of the invention.

FIG. 3 refers to an exemplary flowchart of working principle of portable electrochemical nutrient testing device.

Figure 4:
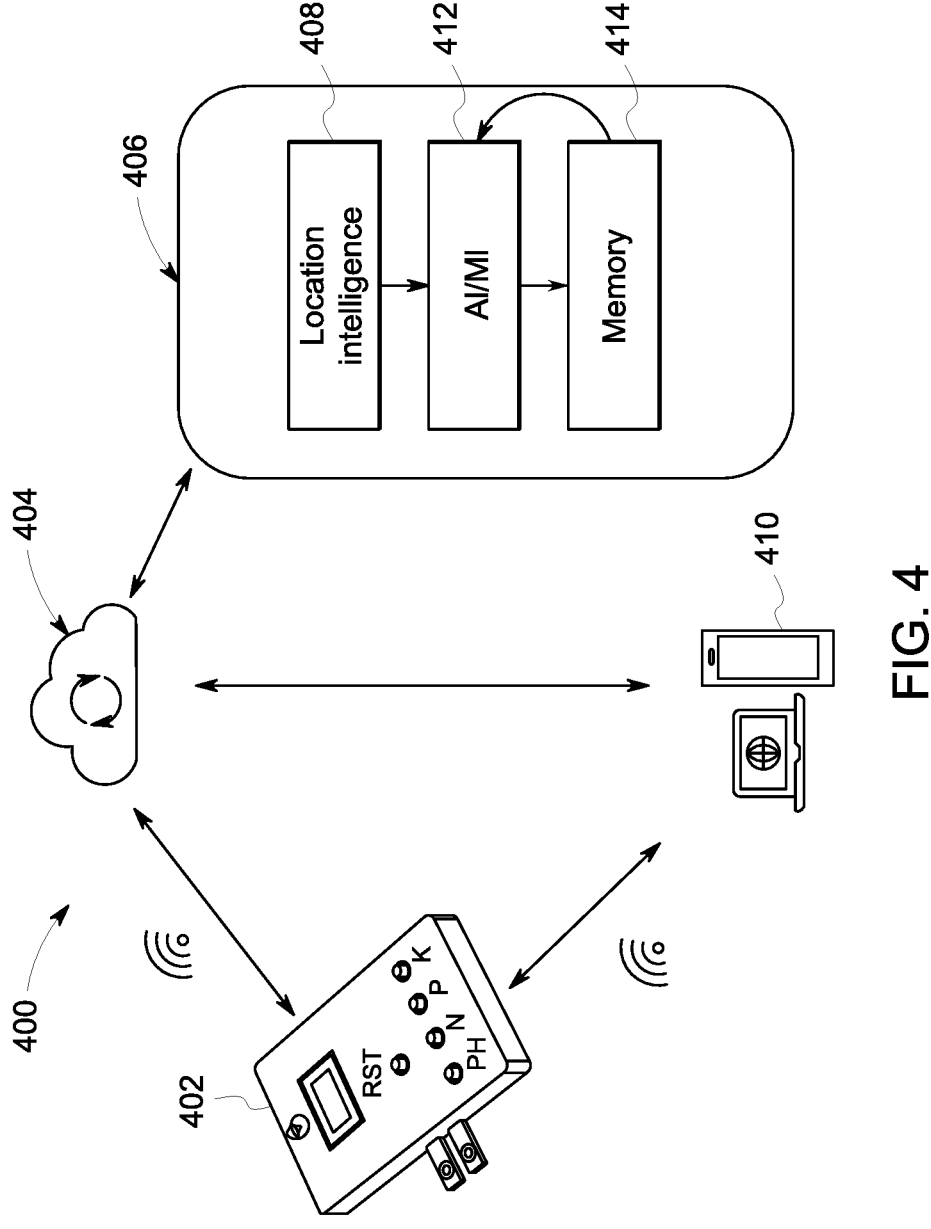
FIG. 4 illustrates an exemplary line diagram of portable electrochemical nutrient testing device for soil health monitoring in accordance to an exemplary embodiment of the invention.

FIG. 4 refers to an exemplary line diagram 400 of portable electrochemical nutrient testing device for soil health monitoring. The screen-printed electrode is a battery-operated system with low power consumption with high accuracy. The electrochemical nutrient testing device 402 is connected to mobile application 410 either through cloud network or independently with the help of Bluetooth, infrared or the like. The cloud network 404 is connected to a processing system 406 which further comprises location intelligence module 408, AL/ML 412, and memory unit 414. The processing system processes the sample and recommends the user regarding soil, water or plant health quality in the form of soil health card using the parameters in the cloud network 404.

Figure 5:
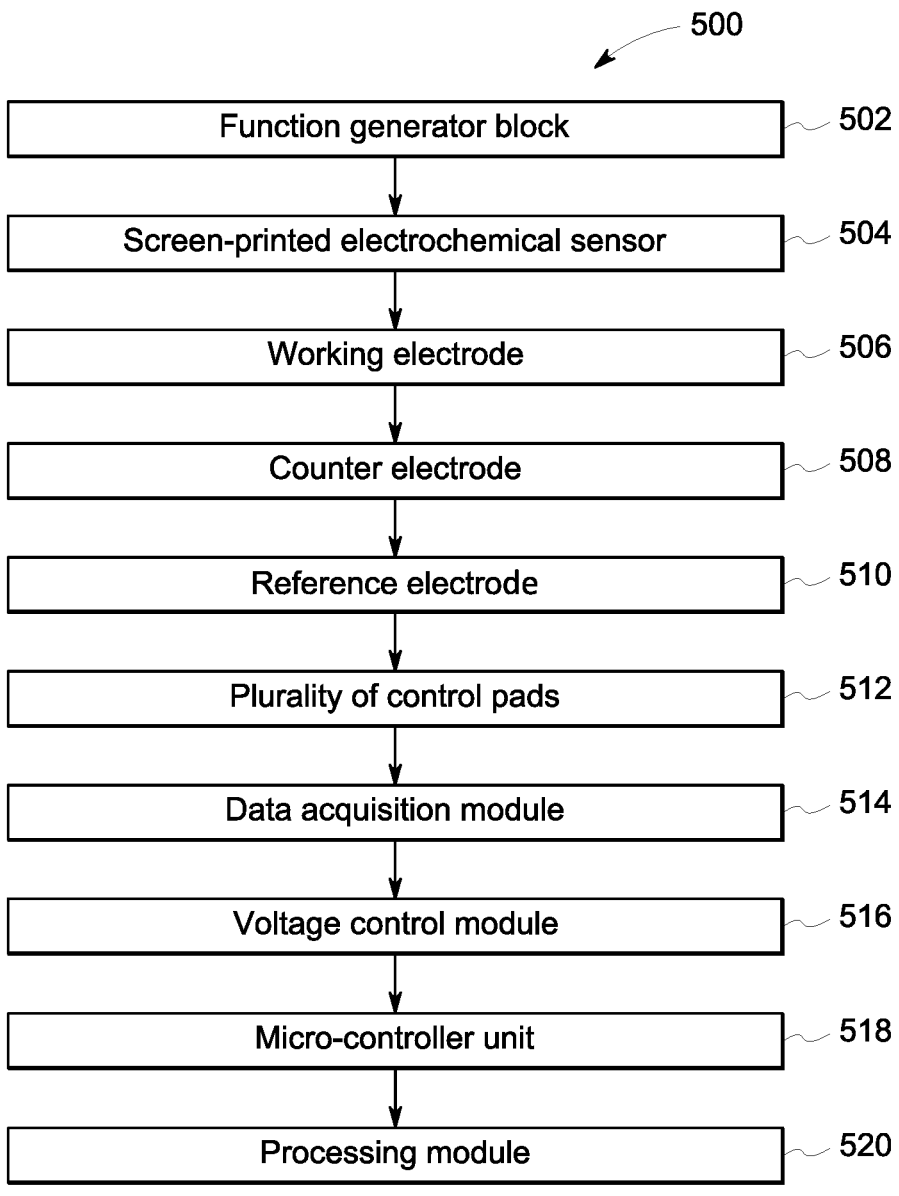
FIG. 5 illustrates various exemplary parts of portable electrochemical nutrient testing device for soil health monitoring in accordance to an exemplary embodiment of the invention.

FIG. 5 refers to various exemplary parts of portable electrochemical nutrient testing device for soil health monitoring. The portable electrochemical nutrient testing device 500 comprises a function generator block 502, screen-printed electrochemical sensor 504, a working electrode 506, a counter electrode 508, a reference electrode 510, plurality of contact pads 512, data acquisition module 514, voltage control module 516, micro-controller unit 518, and processing module 520.

The purpose of the function generator block 502 is to produce the desired square-wave voltammetry signal. The signal is produced by the addition of the square pulse signal with the staircase signal, where both of them have the same frequency. The timer module of the microcontroller unit 518 is used to generate a very low frequency clock signal. The clock signal is given to both block A and block B of the function generator block. The microcontroller unit 518, which is used in the function generator block 502 utilizes less amount of power.

Figure 6:
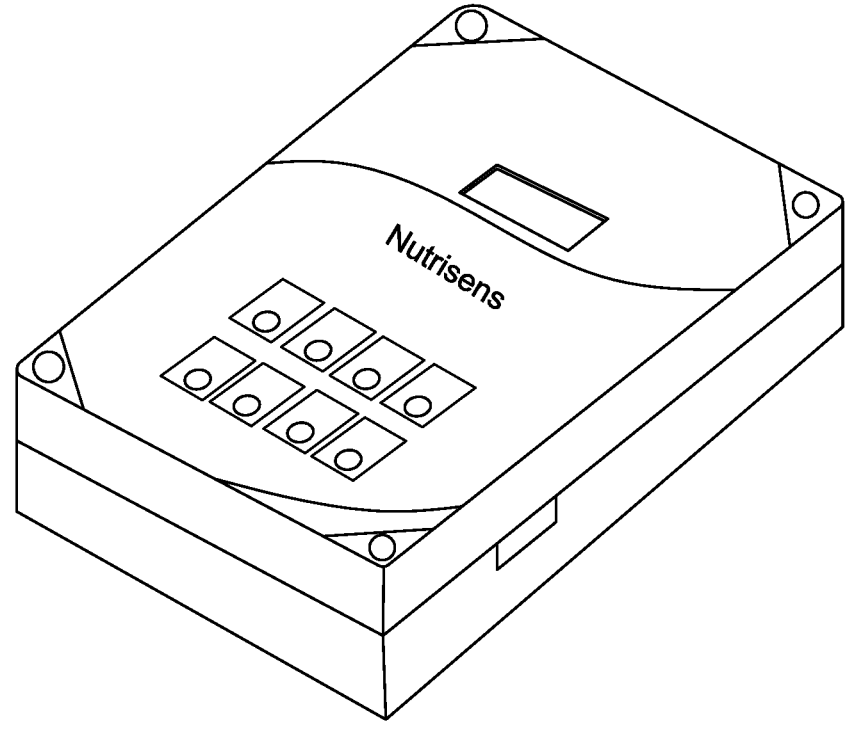
FIG. 6 illustrates an exemplary prototype of portable electrochemical nutrient testing device for soil health monitoring in accordance to an exemplary embodiment of the invention.

FIG. 6 refers to an exemplary prototype of portable electrochemical nutrient testing device for soil health monitoring.

Figure 7:
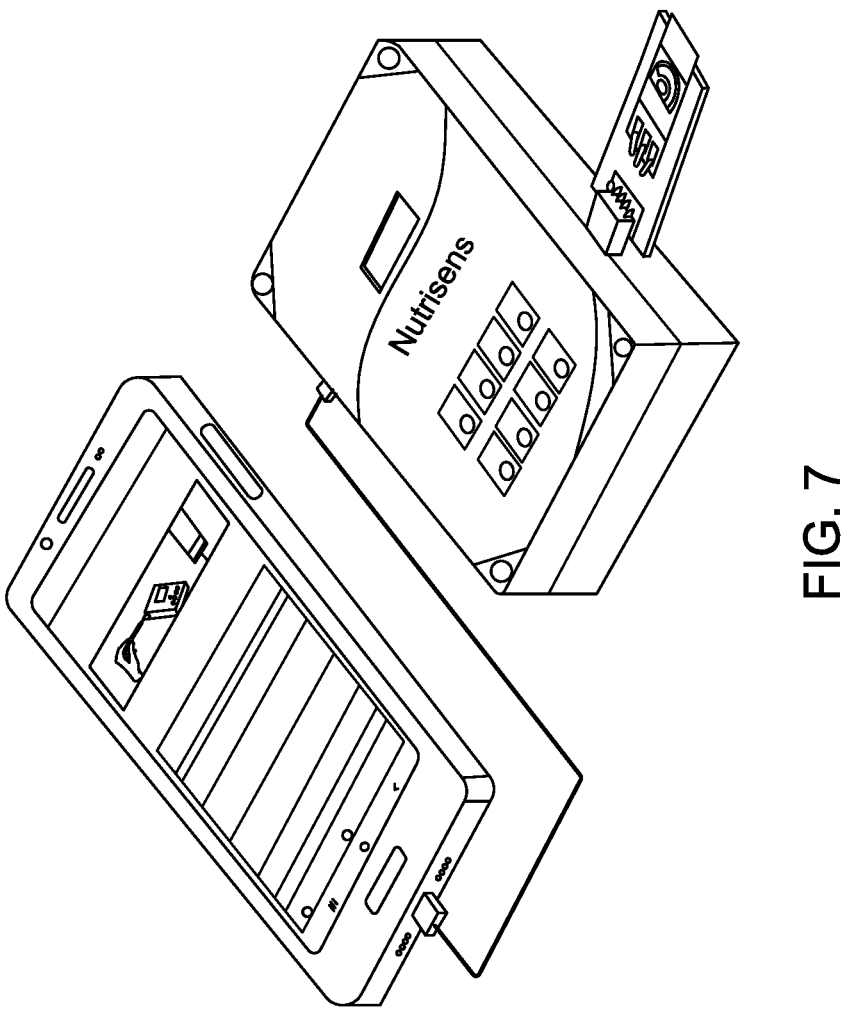
FIG. 7 illustrates an exemplary portable electrochemical nutrient testing device for soil health monitoring connected to a mobile device in accordance to an exemplary embodiment of the invention.

FIG. 7 refers to an exemplary portable electrochemical nutrient testing device for soil health monitoring connected to a mobile device. The portable electrochemical nutrient testing device is connected to the mobile device using either USB, Bluetooth etc. The mobile device is connected to the cloud server in which the sample data gets processed. The processed data is again received by the mobile device which displays the recommendations and results in the form of soil health card.

Figure 8:
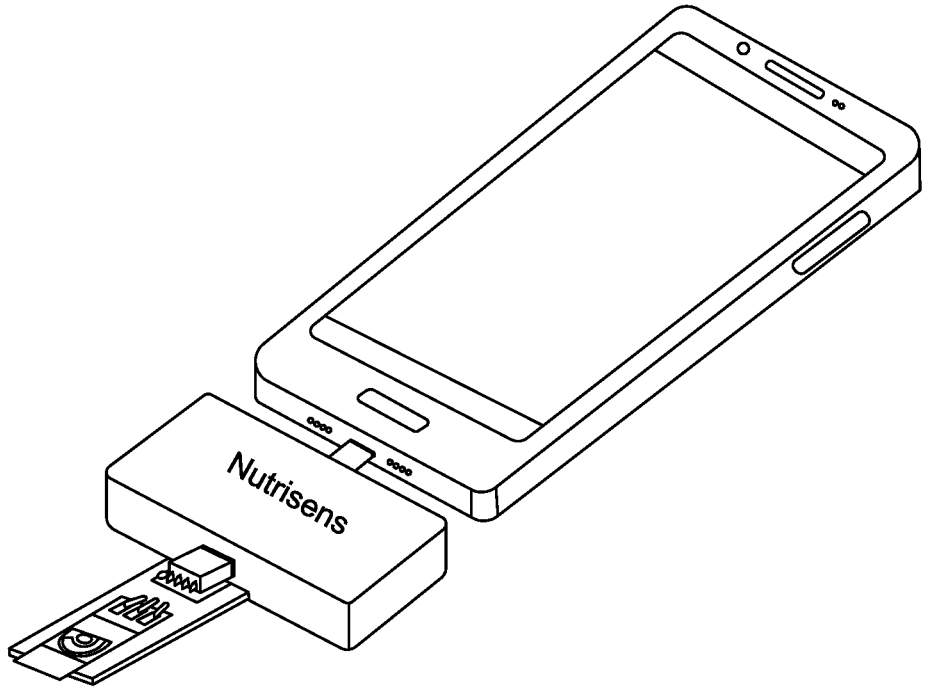
FIG. 8 illustrates an alternate design of electrochemical nutrient testing device and mobile device in accordance to an exemplary embodiment of the invention.

FIG. 8 refers to an alternate design of direct connection between portable electrochemical nutrient testing device and mobile device. The portable electrochemical nutrient testing device is connected directly to the mobile device using a built-in USB port on the portable electrochemical nutrient testing device. A testing strip can be attached on the other side of the portable electrochemical nutrient testing device.

Numerous advantages of the present disclosure may be apparent from the discussion above. In accordance with the present disclosure, a portable electrochemical nutrient testing device for soil health monitoring is disclosed. The portable electrochemical nutrient testing device for soil health monitoring that is designed for in-field nutrient analysis and aids to monitor soil health accurately on a regular basis. The proposed invention aids the farmers to repeatedly evaluate nutrient, electrical conductivity, organic carbon and pH value of soil accurately within less time.

The bio-degradable and paper-based screen printed three-electrode sensor is used to test pH value of the soil. The proposed soil testing device is portable, cost-effective and easy to use. The portable electrochemical nutrient testing device doesn't require prior conditioning and calibration of the electrodes and does not require complex sample preparation using multiple reagents. The proposed portable electrochemical nutrient testing device is cost effective, single handheld device which is easy to operate and is portable.

In the foregoing description various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principles of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

It will readily be apparent that numerous modifications and alterations can be made to the processes described in the foregoing examples without departing from the principles underlying the invention, and all such modifications and alterations are intended to be embraced by this application.

The claimed invention is:

1. A portable electrochemical nutrient testing device, comprising:

a function generator block attached to said electrochemical nutrient testing device configured to produce a change in voltage or current signal;

at least one screen-printed electrochemical sensor configured to test analytes from nutrients derived from a sample, comprising:

a working electrode positioned inside an insulating area appropriately chemically modified to perform an electrochemical reaction when said sample comes in contact with the working electrode;

a counter electrode disposed on a paper substrate and positioned relative to the working electrode to complete an electrochemical circuit;

a reference electrode positioned in said screen-printed electrochemical sensor configured to provide a stable reference potential;

a plurality of contact pads connected to said working electrode, said counter electrode and said reference electrode, wherein the electrochemical nutrient testing device is configured to apply an input waveform generated by the function generator block between said working electrode and said reference electrode, such that current flows between said working electrode and said counter electrode;

a voltage control module connected to said function generator block and said screen-printed electrochemical sensor, wherein the voltage control module is configured to maintain a potential at the working electrode corresponding to the input waveform generated by said function generator block with respect to the reference electrode;

a data acquisition module connected to a voltage difference controller of the voltage control module, wherein the data acquisition module is configured to receive a voltage signal from said voltage difference controller and filter out higher-order harmonics from the voltage signal;

a micro-controller unit connected to said data acquisition module and comprising an analog-to-digital converter configured to receive the filtered voltage signal from the data acquisition module, store the filtered voltage signal as a sample value, and process said sample value to obtain a nutrient content of said sample;

a display unit connected to said micro-controller and configured to display the obtained nutrient content of said sample from the micro-controller, wherein the display unit comprising a portable liquid crystal display (LCD) configured to display soil, water or plant health information based on the nutrient content of said sample;

a location intelligence module configured to store geographical conditions of a location from which the sample is collected; and a processing module configured to receive location intelligence data from the location intelligence module and the nutrient content, and to analyze the location intelligence data and the nutrient content to generate a nutrient map, whereby said electrochemical nutrient testing device is configured for in-field nutrient analysis to monitor soil, water and plant health.

2. The electrochemical nutrient testing device as claimed in claim 1, wherein said voltage control module is a potentiostat.

3. The electrochemical nutrient testing device as claimed in claim 1, wherein said voltage control module maintains the potential at the working electrode with respect to said reference electrode of said screen-printed electrochemical sensor.

4. The electrochemical nutrient testing device as claimed in claim 1, wherein said micro-controller unit is configured to process the voltage signal to separate a faradaic current component from a capacitive current component and to quantify the analyte present in the sample based on the faradaic current component.

5. The electrochemical nutrient testing device as claimed in claim 1, wherein said electrochemical nutrient testing device is configured for use with different agricultural sample types including soil samples, water samples, and plant-derived samples, and wherein the electrochemical nutrient testing device does not require calibration during field use.

6. The electrochemical nutrient testing device as claimed in claim 1, wherein said working electrode of the screen-printed electrochemical sensor is fabricated using a conducting paste selected from a plurality of conducting pastes, wherein the conducting paste is chemically modified to provide selectivity to a selected analyte.

7. The electrochemical nutrient testing device as claimed in claim 6, wherein said plurality of conducting pastes comprises silver, or silver chloride (Ag/AgCl) and carbon paste and is chemically modified to provide selectivity to one or more analytes selected from pH, phosphate, nitrate, potassium, calcium, magnesium, iron, zinc, boron, sulphur, manganese, calcium carbonate, and copper.

8. The electrochemical nutrient testing device as claimed in claim 1, wherein said nutrient content includes information regarding quality of soil, water and plants.

* * * * *